United States Patent
Kato et al.

(10) Patent No.: US 6,261,798 B1
(45) Date of Patent: Jul. 17, 2001

(54) METHODS FOR PRODUCING [S,S]-ETHYLENEDIAMINE-N,N'-DISUCCINATE

(75) Inventors: Osamu Kato; Makoto Kaneko; Takakazu Endo, all of Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/582,171

(22) PCT Filed: Dec. 22, 1998

(86) PCT No.: PCT/JP98/05826

§ 371 Date: Jun. 22, 2000

§ 102(e) Date: Jun. 22, 2000

(87) PCT Pub. No.: WO99/32650

PCT Pub. Date: Jul. 1, 1999

(30) Foreign Application Priority Data

Dec. 22, 1997 (JP) .............................. 364798/1998

(51) Int. Cl.[7] .............. C12P 13/02; C12P 39/00
(52) U.S. Cl. ............ 435/42; 435/128; 435/170; 435/232; 435/252.1; 435/252.31; 435/252.34; 435/252.5; 435/252.4; 435/253.3; 435/252.3
(58) Field of Search ............... 435/128, 42, 170, 435/232, 252.31, 252.34, 252.5, 253.3, 252.3, 252.1, 252.4

(56) References Cited

U.S. PATENT DOCUMENTS 5,707,836 * 1/1998 Endo et al. ................. 435/109
5,939,296 * 8/1999 Sakano et al. ............. 435/145
5,981,238 * 11/1999 Kaneko et al. ............. 435/106
6,103,508 * 8/2000 Kato et al. ................. 435/184

FOREIGN PATENT DOCUMENTS

805211A2 * 11/1997 (EP) .
8-51989 * 2/1996 (JP) .
9-140390 * 6/1997 (JP) .
9-289895 * 11/1997 (JP) .
10-259170 * 9/1998 (JP) .

OTHER PUBLICATIONS

Computer Caplus Abstract 2000:405851 Kujira et al. JP2000169434 Pub Dec. 8, 1998.*

* cited by examiner

Primary Examiner—Herbert J. Lilling
(74) Attorney, Agent, or Firm—Oblon, Spivak, McClelland, Maier & Neustadt, P.C.

(57) ABSTRACT

The present invention relates to a method of producing [S,S]-ethylenediamine-N,N'-disuccinate wherein a microorganism having malate isomerase activity or matter processed therefrom and a microorganism having ethylenediamine-N,N'-disuccinate ethylenediamine lyase activity or matter processed therefrom are allowed to act on a substrate solution containing maleic acid, maleic anhydride, or a maleic acid salt, and ethylenediamine, in the presence of at least one metal ion selected from the group consisting of alkaline earth metals, iron, zinc, copper, nickel, aluminum, titanium and manganese. The present invention enables to accumulate [S,S]-ethylenediamine-N,N'-disuccinate in a higher yield and at a high concentration within a reaction system using maleic acid as a raw material.

25 Claims, No Drawings

METHODS FOR PRODUCING [S,S]-ETHYLENEDIAMINE-N,N'-DISUCCINATE

This application is a 371 of PCT/JP98/05826 Dec. 22, 1998.

BACKGROUND OF THE INVENTION

1. Technical Field of the Invention

The present invention relates to a method of producing [S,S]-ethylenediamine-N,N'-disuccinate (hereinafter abbreviated as [S,S]-EDDS). More specifically, the present invention relates to a method of producing [S,S]-EDDS from maleic acid, maleic anhydride or maleic acid salt and ethylenediamine by action of microorganisms or enzymes.

2. Disclosure of the Related Art

[S,S]-EDDS has the high ability to capture heavy metals and is bio-degradable when released into the nature. Hence [S,S]-EDDS is expected to be used as a bleaching agent for photography, an electroless plating agent, or a builder for detergent.

The present inventors have already proposed methods of producing [S,S]-EDDS by microorganisms: (1) a method of producing [S,S]-EDDS from fumaric acid and ethylenediamine (JP-A-9-140390, U.S. Pat. No. 5,707,836, and European Patent No. 0731171), (2) a method of producing the same from maleic acid and ethylenediamine (JP-A-9-289895) and the method of (1) under the presence of metal ion (European Patent No. 0805211, JP-A-10-52292).

In terms of raw materials, the method of (2) has the advantage of providing a more economical method of manufacturing [S,S]-EDDS, since fumaric acid is industrially produced from maleic acid through an isomerization process by chemical methods (U.S. Pat. Nos. 2,816,923, 2,955,136, and 2,332,992).

The method disclosed in JP-A-9-289895, wherein maleic acid and ethylenediamine are used as substrates, is not a sufficient method because of its low yields.

Accordingly, an object of the present invention is to obtain [S,S]-EDDS in high yield using maleic acid as a raw material.

The present inventors have intensively investigated an application of malate isomerase (JP2664648, JP-A-8-51989, and European Patent No. 693557) to the production of [S,S]-EDDS. There are many biochemical studies about malate isomerase (W. Scher et al., J. Biol. chem., 244, 1878–1882 (1969), Y. Takamura et al., Agr. Biol. Chem., 33, 718–728 (1969), T. Kimura et al., Agr. Biol. Chem., 50, 89–94 (1986), and T. Nakajima-Kambe et al., J. Ferment. Bioeng., 84, 165–168 (1997)). Moreover, the malate isomerase has been proposed for the production of aspartic acid.

The present inventors have now found that the addition of both a microorganism having malate isomerase activity and a microorganism having ethylenediamine-N,N'-disuccinate ethylenediamine lyase (hereinafter referred to as EDDSase) activity to a solution containing maleic acid and ethylenediamine in the presence of a metal ion e.g., alkaline earth metal can largely increase the conversion rate of maleic acid to [S,S]-EDDS, although the addition of only these microorganisms to the solution results in a low conversion rate to [S,S]-EDDS.

SUMMARY OF THE INVENTION present invention provides a method of producing [S,S]-ethylenediamine-N,N'-disuccinate, wherein a microorganism having malate isomerase activity or matter processed therefrom and a microorganism having ethylenediamine-N, N'-disuccinate ethylenediamine lyase activity or matter processed therefrom are allowed to act on a substrate solution containing maleic acid, maleic anhydride, or maleic acid salt, and ethylenediamine, in the presence of at least one metal ion selected from the group consisting of alkaline earth metals, iron, zinc, copper, nickel, aluminum, titanium and manganese ions, thereby obtaining [S,S]-ethylenediamine-N,N'-disuccinate.

High-yield production of [S,S]-EDDS is impossible when using only the presence of an enzyme converting maleic acid into fumaric acid and an enzyme converting fumaric acid into [S,S]-EDDS, because both enzymes catalyze a reversible equilibrium reaction independent of their source. However in the present invention, it is assumed that [S,S]-EDDS is changed into a metal complex in the presence of a metal ion such as an alkaline earth metal ion and shifted out of the enzymatic reaction system so that the reaction equilibrium is driven toward the production side, thereby accumulating a high concentration of [S,S]-EDDS in a high yield within the reaction system.

The conversion reactions from maleic acid into fumaric acid and from fumaric acid into [S,S]-EDDS are weak exothermic reactions. Thermodynamically, as the reaction temperature becomes lower, the equilibrium shifts to the side of producing fumaric acid. Thus in the reaction, in the absence of the metal ion as described above, manipulations such as lowering the reaction temperature in the latter period of the reaction are required to improve the yield. However, the presence of the metal ion can lead to high conversion yield without such manipulations.

The specification includes all or part of the contents as disclosed in the specification and/or drawings of Japanese Patent Application No. 9-364798 (filed on Dec., 22th, 1997), which is a priority claimed in the present application.

DETAILED DESCRIPTION OF THE INVENTION

The present invention will now be described in detail.

Metal ions used in the present invention include alkaline earth metals, iron, zinc, copper, nickel, aluminum, titanium and manganese ions. For example, Mg(II), Ca(II), Sr(II), Ba(II), Fe(II), Fe(III), Zn(II), Cu(II), Ni(II), Al(III), Ti(IV), and Mn(II) ions, and various complex ions thereof can be included.

Ion sources of these metals can include hydroxides and oxides of these metals, salts of inorganic or organic acids, e.g., sulfuric acid, hydrochloric acid, nitric acid, phosphoric acid, carbonic acid and acetic acid, minerals containing these metallic compounds, and compounds with maleic acid and ethylenediamine that are substrates of the present invention. Two or more of the compounds may be mixed for use in the present invention.

These metallic compounds vary in their solubility in water, some have low and some have slight water solubility. Both types of these compounds can be used in the present invention, because most of them are solubilized by a coordination ability of [S,S]-EDDS even when these compounds are present at more than saturation concentration, for example in a suspension state. In other words, any compound can be used as a source of "metallic ions" in the present invention so far as the metallic ion can coordinate to [S,S]-EDDS, by which the advantages of the present invention can be achieved.

Any microorganisms capable of isomerizing maleic acid into fumaric acid can be used as those having a malate isomerase activity in the present invention. These microorganisms may belong to, but not limited to, the genus Alcaligenes, the genus Pseudomonas, the genus Xanthomonas, and the genus Bacillus. Further genetically engineered recombinant microorganisms having malate isomerase genes from the above-mentioned microorganisms can be used as well.

Specific examples of strains for use in the present invention include, but not limited to, *Alcaligenes faecalis* IFO 12669, IFO 13111 and IAM 1473, *Alcaligenes eutrophus* IAM 12305, *Pseudomonas fluolescens* ATCC 23728, *Xanthomonas maltophilia* ATCC 13270, Bacillus sp. MI105 (FERM BP-5164), *Bacillus stearothermophirus* MI101 (FERM BP-5160) and MI102 (FERM BP-5161), *Bacillus brevis* MI103 (FERM BP-5162) and MI104 (FERM BP-5163).

These microorganisms are available from Institute for Fermentation (IFO), Osaka, Japan; IAM Culture Collection, Cell/Functional Polymer Center, Cell Biology, the University of Tokyo, Japan, and American Type Culture Collection (ATCC).

Any microorganisms capable of producing [S,S]-EDDS from fumaric acid and ethylenediamine can be used as those having EDDSase activity in the present invention. These microorganisms can include, but not limited to, the genus Brevundimonas, the genus Paracoccus, the genus Sphingomonas, the genus Acidovorax, the genus Pseudomonas, and the genus Burkholderia. Further, genetically engineered recombinant microorganisms having EDDSase genes from these microorganisms can also be used.

Specific examples of the strains can include, but not limited to, Brevundimonas sp. TN-3 (FERM BP-5886) and TN-30 (FERM BP-5417), Paracoccus sp. KK-6 (FERM BP-5415), Sphingomonas sp. TN-28 (FERM BP-5419), Acidovorax sp. TN-51 (FERM BP-5416), Pseudomonas sp. TN-131 (FERM BP-5418), Burkholderia sp. KK-5 (FERM BP-5412) and KK-9 (FERM BP-5413). Specific examples of the genetically engineered microorganisms include, but not limited to, transformants: *E.coli* JM109/pEDS020 (FERM BP-6161), and *Rhodococcus rhodochrous* ATCC 17895/pSE 001 (FERM BP-6548). These transformants are obtained by introducing a gene DNA encoding EDDSase derived from the Brevundimonas sp. TN-3, into *Escherichia coli* JM109 (ATCC 53323) and *Rhodococcus rhodochrous* ATCC 17895.

These microorganisms having EDDSase activity have been deposited with National Institute of Bioscience and Human Technology, Agency of Industrial Science and Technology (1–3, Higashi 1-chome, Tsukuba-shi, Ibaraki-ken, Japan). Their mycological features are described in JP-A-9-140390 and European Patent No. 0805211. The transformants of interest can be obtained according to the production methods disclosed in JP-A-10-210984 and Japanese Patent Application No. 9-311046.

Culture of the microorganism used in the present invention can be performed using usual media, which contain an assimilable carbon source (e.g., glycerol, glucose, or saccharose), nitrogen source (e.g., inorganic ammonium salt or nitrate, casamino acid, meat extract, yeast extract, or corn steep liquor), and essential ingredients for growth of each microorganism, such as inorganic salts (e.g., magnesium chloride, calcium chloride, manganese sulfate, iron chloride, and zinc sulfate), vitamines, and nucleic acids. Addition of maleic acid and [S,S]-EDDS to the culture medium is preferred because it can result in increased malate isomerase activity and EDDSase activity.

The culture medium preferably has a pH of 4 to 10, preferably 6 to 9. The culture temperature ranges from 20° C. to 90° C., preferably from 25° C. to 80° C. Culture can be conducted aerobically for 1 to 14 days.

The [S,S]-EDDS production reaction can be conducted as follows.

0.01 to 5 weight % each or preferably 0.1 to 2 weight % each of a microorganism (cell) having malate isomerase activity, from which enzyme activity involving side reactions, e.g. fumarase, is removed, or a matter processed from the microorganism (e.g., disrupted microbial cells, crude enzyme solution, purified enzyme solution, immobilized microbial cells, or immobilized enzyme); and a microorganism (or microbial cell) having EDDSase activity or matter processed from the microorganism (e.g., disrupted microbial cells, crude enzyme solution, purified enzyme solution, immobilized microbial cells, or immobilized enzyme), are added to an aqueous medium at a pH of 4 to 11, preferably 6 to 10, containing 0.01M to the saturated concentration, preferably 0.02M to 1.2M, maleic acid, maleic anhydride or a maleic acid salt, and 0.01M to 2M, preferably 0.015M to 1M ethylenediamine. Further the above-described metallic compound is added to the mixture in an amount of 0.01 to 2 times greater in mole (as the metal) than the theoretical amount of [S,S]-EDDS to be produced. Then the mixture is allowed to react at a reaction temperature of 5° C. to 60° C., preferably 10° C. to 55° C., for 0.5 to 48 hours.

To collect a [S,S]-metal complex from the reaction mixture after completion of the reaction, several procedures to obtain the compound of interest are employed. These procedures include the reaction in the presence of a certain metallic ion, pH preparation, concentration and other procedures.

To collect [S,S]-EDDS from the reaction mixture after completion of the reaction, usually precipitation using mineral acid is performed. However in the system forming a stable complex at a pH fro the acid precipitation, for example when the reaction is conducted in the presence of a heavy metal ion, e.g. iron ion, an additional procedure to remove the metal ion is needed before the acid precipitation. Therefore in production of [S, S]-EDDS, it is effective to perform the reaction in the presence of an ion of alkaline earth metal (e.g. magnesium or calcium), which requires no such an additional procedure upon acid precipitation.

Now the present invention will be further explained in detail according to, but not limited to, the following examples.

EXAMPLES

Example 1

(1) Preparation of Microbial Cells Having Malate Isomerase Activity

Each strain of *Alcaligenes faecalis* IFO 12669, IFO 13111 and IAM 1473, *Alcaligenes eutrophus* IAM 12305 and *Pseudomonas fluolescens* ATCC 23728 was shake-cultured in 1 L of a medium containing maleic acid (per liter of the medium; 5 g of sodium malate, 10 g of meat extract, 5 g of yeast extract, 5 ml of a solution of metal salt mixture, 50 mM phosphate buffer, pH 7.0) at 30° C. for 2 to 3 days. The cells were centrifuged at 10,000 rpm for 20 minutes, and then washed with 1 L of 50 mM phosphate buffer (pH 8.5), thereby preparing 100 ml of a cell suspension in the same buffer.

| The metal salt mixture solution has a composition as follows (per 100 ml): | |
|---|---|
| Magnesium chloride 6H₂O | 8 g |
| Calcium chloride | 0.8 g |
| Manganese sulfate 6H₂O | 0.6 g |
| Ferric chloride 6H₂O | 0.12 g |
| Zinc sulfate | 0.06 g |

(2) Preparation of Microbial Cells Having EDDSase Activity

Brevundimonas sp. TN-3 was shake-cultured in 2 L of a medium containing [S,S]-EDDS (per liter of the medium; 2 g of [S,S]-EDDS, 2 g of glucose, 1 g of yeast extract, 0.5 g of polypeptone, 1 g of magnesium sulfate 7H₂O, 0.28 g of sodium sulfate, 0.5 ml of a solution of metal salt mixture, 25 mM phosphate buffer, pH7.5) at 30° C. for 3 days. The cells were centrifuged at 10,000 rpm for 20 minutes and suspended in 500 ml of 100 mM borate buffer (pH of 9.2). After that for heat treatment, the suspension was left in a water bath at 45° C. for 4 hours. The cells were collected by centrifugation at 10,000 rpm for 20 minutes. The collected cells were washed once with 500 ml of 50 mM phosphate buffer at a pH of 8.5, thereafter 100 ml of a cell suspension was prepared using the same buffer.

(3) [S,S]-EDDS Production Reaction

Five ml of the cell suspension obtained from the microorganism having malate isomerase activity and 5 ml of the cell suspension from that having EDDS lyase activity were added to 100 ml of a substrate solution containing 300 mM maleic acid, 100 mM ethylenediamine, 150 mM magnesium hydroxide. The mixture was allowed to react at 35° C. for a period of 14 to 20 days until the production of [S,S]-EDDS ceases. For comparison, a similar experiment was conducted using a substrate solution containing no magnesium hydroxide.

In this production reaction, the pH was controlled within a range from 8.3 to 8.8 by a pH controller using sodium hydroxide since the [S,S]-EDDS production reaction in the presence of magnesium hydroxide is accompanied by decrease decrease in pH during the reaction.

(4) Determination of [S,S]-EDDS and Analysis of Optical Purity

The insoluble matter in the solution after the completion of reaction was removed by centrifugation at 15,000 rpm at 5° C. for 5 minutes. Then the supernatant was determined for a level of the produced [S, S]-EDDS by liquid chromatography (column; WAKOSIL 5C8 (Wako Pure Chemical Industries., Ltd.), effluent; 10 mM tetra-n-butyl ammonium hydroxide, 0.4 mM CuSO₄, 50 mM phosphoric acid, pH 2). Further the optical purity of the [S,S]-EDDS was analyzed by liquid chromatography (column; MCI GEL CRS 10W (Mitsubishi Chemical Corp.), effluent; 10 mM copper sulfate). For determination of the metallic complex, sodium hydroxide was added at a final concentration of 1.5% to the reaction-completed solution, from which insoluble matter was removed, and the mixture was allowed to stand at room temperature for 30 minutes. After insoluble hydroxide was removed by centrifugation, the pH was controlled to 7.5 using phosphoric acid. Then an amount and an optical purity of the [S,S]-EDDS were analyzed.

(5) Results

TABLE 1

| A† | B‡ | Mg(OH)₂ | Amount of [S,S]-EDDS produced ¶ (mM) | Optical purity of [S,S]-EDDS (% ee) |
|---|---|---|---|---|
| IFO12669 | TN-3 | − | 37 | >99 |
|  |  | + | 92 | >99 |
| IFO13111 | TN-3 | + | 90 | >99 |
| IAM1473 | TN-3 | + | 91 | >99 |
| IAM12305 | TN-3 | − | 43 | >99 |
|  |  | + | 93 | >99 |
| ATCC23728 | TN-3 | − | 38 | >99 |
|  |  | + | 89 | >99 |

†A: Microorganism having malate isomerase activity
‡B: Microorganism having EDDSase activity
¶: The amount of [S,S]-EDDS produced is a value corrected for the dilution of the reaction solution by addition of the alkaline and phosphoric acid.

Example 2

(1) Preparation of Microbial Cells

Cell suspensions were prepared in the same manner as in Example 1 by individually culturing the microorganism having malate isomerase activity, Alcaligenes faecalis IFO 12669, and that having EDDSase activity, that is, Burkholderia sp. KK-5, Paracoccus sp. KK-6, Brevundimonas sp. TN-3, Sphingomonas sp. TN-28, Acidovorax sp. TN-51 and Pseudomonas sp. TN-131 strains.

(2) [S,S]-EDDS Production Reaction

Five ml of the microorganism (IFO 12669) having malate isomerase activity and 5 ml of each microorganism (KK-5, KK-6, TN-3, TN-28, TN-51 or TN-131) having EDDSase were added in the form of suspension to the same substrate solution (300 mM maleic acid, 100 mM ethylenediamine, 150 mM magnesium hydroxide, pH 8.5) as in Example 1. The mixture was allowed to react for a period of 14 to 20 days at 35° C. until the production of [S,S]-EDDS ceases. For comparison, a similar experiment was conducted using substrate solution containing no magnesium hydroxide.

(3) Determination of [S,S]-EDDS and Analysis of the Optical Purity

The insoluble matter in the solution after the completion of reaction was removed by centrifugation at 15,000 rpm at 5° C. for 5 minutes. Then the supernatant was determined for a level of the produced [S,S]-EDDS by liquid chromatography (column; WAKOSIL 5C8 (Wako Pure Chemical Industries., Ltd.), effluent; 10 mM tetra-n-butyl ammonium hydroxide, 0.4 mM CuSO₄, 50 mM phosphoric acid, pH 2). Further the optical purity of the [S,S]-EDDS was analyzed by liquid chromatography (column; MCI GEL CRS 10W (Mitsubishi Chemical Corp.), effluent; 10 mM copper sulfate). For determination of the metal complex, sodium hydroxide was added at a final concentration of 1.5% to the reaction-completed solution, from which insoluble matter was removed, and the mixture was allowed to stand at room temperature for 30 minutes. After insoluble hydroxide was removed by centrifugation, the pH was controlled to 7.5 using phosphoric acid. Then an amount and an optical purity of the produced [S,S]-EDDS were analyzed.

(4) Results

TABLE 2

| A† | B‡ | Mg(OH)$_2$ | Amount of [S,S]-EDDS produced ¶ (mM) | Optical purity of [S,S]-EDDS (% ee) |
|---|---|---|---|---|
| IFO12669 | KK-5 | Not added | 40 | >98 |
| | | Added | 88 | >98 |
| | KK-6 | Not added | 41 | >98 |
| | | Added | 90 | >98 |
| | TN-3 | Not added | 43 | >98 |
| | | added | 91 | >98 |
| | TN-28 | Not added | 41 | >98 |
| | | added | 91 | >98 |
| | TN-51 | Not added | 44 | >98 |
| | | added | 87 | >98 |
| | TN-131 | Not added | 42 | >98 |
| | | added | 91 | >98 |

†A: Microorganism having malate isomerase activity
‡B: Microorganism having EDDSase activity
¶: The amount of [S,S]-EDDS produced is a value corrected for the dilution of the reaction solution by addition of the alkaline and phosphoric acid.

Example 3

(1) Preparation of Microbial Cells

Cell suspensions were prepared in the same manner as in Example 1 by individually culturing *Alcaligenes faecalis* IFO 12669, which is a microorganism containing malate isomerase, and Brevundimonas sp. TN-3 strain, a microorganism containing EDDSase.

(2) [S,S]-EDDS Production Reaction

Five ml of the suspension of IFO 12669 and 5 ml of the suspension of TN-3 were added to 100 ml of a substrate solution (pH 8.5) containing 300 mM maleic acid, 100 mM ethylenediamine and 150 mM hydroxide (magnesium hydroxide, calcium hydroxide, titanium hydroxide, manganese hydroxide, zinc hydroxide, aluminum hydroxide, or ferric hydroxide). (Note: magnesium hydroxide and calcium hydroxide are soluble at this pH; other hydroxides are insoluble) The mixture was allowed to react for a period of 14 to 20 days at 35° C. until the production of [S,S]-EDDS ceases. For comparison, a similar experiment was conducted using a substrate solution containing no hydroxide.

(3) Determination of [S,S]-EDDS and Analysis of the Optical Purity

The insoluble matter in the solution after the completion of reaction was removed by centrifugation at 15,000 rpm at 5° C. for 5 minutes. Then the supernatant was determined for a level of the produced [S,S]-EDDS by liquid chromatography (column; WAKOSIL 5C8 (Wako Pure Chemical Industries., Ltd.), effluent; 10 mM tetra-n-butyl ammonium hydroxide, 0.4 mM CuSO$_4$, 50 mM phosphoric acid, pH 2). Further the optical purity of the [S,S]-EDDS was analyzed by liquid chromatography (column; MCI GEL CRS 10W (Mitsubishi Chemical Corp.), effluent; 10 mM copper sulfate). For determination of the metal complex, sodium hydroxide was added at a final concentration of 1.5% to the reaction-completed solution, from which insoluble matter was removed, and the mixture was allowed to stand at room temperature for 30 minutes. After insoluble hydroxide was removed by centrifugation, the pH was controlled to 7.5 using phosphoric acid. Then an amount and an optical purity of the produced [S,S]-EDDS were analyzed.

(4) Results

TABLE 3

| Hydroxide | Amount of [S,S]-EDDS produced ¶ (mM) |
|---|---|
| Not added | 42 |
| Magnesium hydroxide | 88 |
| Calcium hydroxide | 80 |
| Aluminum hydroxide | 76 |
| Titanium hydroxide | 85 |
| Manganese hydroxide | 92 |
| Ferric hydroxide | 84 |
| Zinc hydroxide | 79 |

¶: The amount of [S,S]-EDDS produced is a value corrected for the dilution of the reaction solution by addition of the alkaline and phosphoric acid.

All publications, patents and patent applications cited herein are incorporated herein by reference in their entirety. It will be apparent to one skilled in the art that any variations and modifications can be made therein without departing from the spirit and scope thereof.

What is claimed is:

1. A method of producing [S,S]- ethylenediamine-N, N'-disuccinate wherein a microorganism having malate isomerase activity or matter having malate isomerase activity processed from said microorganism and a microorganism having ethylenediamine-N, N'- disuccinate ethylenediamine lyase activity or matter having ethylenediamine-N, N'-disuccinate ethylenediamine lyase activity processed from said microorganism are allowed to act on a substrate solution containing maleic acid, maleic anhydride, or a maleic acid salt, and ethylenediamine, in the presence of at least one metal ion selected from the group consisting of alkaline earth metals, iron, zinc, copper, nickel, aluminum, titanium and manganese ions, obtaining [S,S]-ethylenediamine-N, N'-disuccinate.

2. The method of claim 1 wherein the microorganism having malate isomerase activity or matter having malate isomerase activity processed from said microorganism is selected from the group consisting of microorganisms belonging to the genus Alcaligenes, the genus Pseudomonas, the genus Xanthomonas and the genus Bacillus; genetically engineered recombinant microorganisms having malate isomerase genes from said microorganisms; and matter having malate isomerase activity processed from said microorganisms.

3. The method of claim 1 wherein the microorganism having ethylenediamine-N, N'-disuccinate ethylenediamine lyase activity or matter having ethylenediamine-N, N'-disuccinate ethylenediamine lyase activity processed from said microorganism is selected from the group consisting of microorganisms belonging to the genus Brevundimonas, the genus Paracoccus, the genus Sphingomonas, the genus Acidovorax, the genus Pseudomonas, and the genus Burkholderia; genetically engineered recombinant microorganisms having ethylenediamine-N, N'-disuccinate ethylenediamine lyase genes from said microorganisms; and matter having ethylenediamine-N, N'-disuccinate ethylenediamine lyase activity processed from said microorganisms.

4. The method of claim 1 wherein the matter processed from said microorganism having said activity is selected from the group consisting of disrupted microbial cells, crude enzyme solution, purified enzyme solution, immobilized microbial cells, and immobilized enzyme.

5. The method of any one of claims 1 to 4 wherein the maleic acid, maleic anhydride, or a maleic acid salt has a concentration ranging from 0.01M to the saturated concentration.

6. The method of any one of claims 1 to 4 wherein the ethylenediamine has a concentration ranging from 0.01M to 2M.

7. The method of any one of claims 1 to 4 wherein the metal ion is added in an amount of 0.01 to 2 times greater in moles than the theoretical amount of [S,S]-ethylenediamine-N,N'-disuccinate which produces a metallic compound.

8. The method of any one of claims 1 to 4 wherein the reaction is conducted in an aqueous medium with a pH of 4 to 11.

9. The method of any one of claims 1 to 4 wherein the reaction is conducted at a temperature from 5° C. to 60° C.

10. A method of producing [S,S]-ethylenediamine-N,N'-disuccinate according to claim 1, wherein a microorganism having malate isomerase activity and a microorganism having ethylene diamine-N,N'-disuccinate ethylenediamine lyase activity are allowed to act on a substrate solution containing maleic acid, maleic anhydride, or a maleic acid salt, and ethylenediamine, in the presence of at least one metal ion selected from the group consisting of alkaline earth metals, iron, zinc, copper, nickel, aluminum, titanium and manganese ions, obtaining [S,S]-ethylenediamine-N,N'-disuccinate.

11. A method of producing [S,S] ethylenediamine-N,N'-disuccinate according to claim 1, wherein a microorganism having malate isomerase activity and matter having ethylenediamine-N,N'-disuccinate ethylenediamine lyase activity processed from a microorganism having ethylenediamine-N,N'-disuccinate ethylenediamine lyase activity are allowed to act on a substrate solution containing maleic acid, maleic anhydride, or a maleic acid salt, and ethylenediamine, in the presence of at least one metal ion selected from the group consisting of alkaline earth metals, iron, zinc, copper, nickel, aluminum, titanium and manganese ions, obtaining [S,S]-ethylenediamine-N,N'-disuccinate.

12. A method of producing [S,S]-ethylenediamine-N,N'-disuccinate according to claim 1, wherein matter having malate isomerase activity processed from a microorganism having malate isomerase activity and a microorganism having ethylenediamine-N,N'-disuccinate ethylenediamine lyase activity are allowed to act on a substrate solution containing maleic acid, maleic anhydride, or a maleic acid salt, and ethylenediamine, in the presence of at least one metal ion selected from the group consisting of alkaline earth metals, iron, zinc, copper, nickel, aluminum, titanium and manganese ions, obtaining [S,S]-ethylenediamine-N,N'-disuccinate.

13. A method of producing [S,S]-ethylenediamine-N,N'-disuccinate according to claim 1, wherein matter having malate isomerase activity processed from a microorganism having malate isomerase activity and matter having ethylenediamine-N,N'-disuccinate ethylenediamine lyase activity processed from a microorganism having ethylenediamine-N,N'-disuccinate ethylenediamine lyase activity are allowed to act on a substrate solution containing maleic acid, maleic anhydride, or a maleic acid salt, and ethylenediamine, in the presence of at least one metal ion selected from the group consisting of alkaline earth metals, iron, zinc, copper, nickel, aluminum, titanium and manganese ions, obtaining [S,S]-ethylenediamine-N,N'-disuccinate.

14. The method of claim 10 wherein the microorganism having malate isomerase activity is selected from the group consisting of microorganisms belonging to the genus Alcaligenes, the genus Pseudomonas, the genus Xanthomonas, the genus Bacillus and genetically engineered recombinant microorganisms having malate isomerase genes from said microorganisms.

15. The method of claim 10 wherein the microorganism having ethylenediamine-N, N'-disuccinate ethylenediamine lyase activity is selected from the group consisting of microorganisms belonging to the genus Brevundimonas, the genus Paracoccus, the genus Sphingomonas, the genus Acidovorax, the genus Pseudomonas, the genus Burkholderia and genetically engineered recombinant microorganisms having ethylenediamine-N,N'-disuccinate ethylenediamine lyase genes from said microorganisms.

16. The method of claim 10 wherein the microorganism having malate isomerase activity is selected from the group consisting of microorganisms belonging to the genus Alcaligenes, the genus Pseudomonas, the genus Xanthomonas, the genus Bacillus and genetically engineered recombinant microorganisms having malate isomerase genes from said microorganisms and the microorganism having ethylenediamine-N,N'-disuccinate ethylenediamine lyase activity is selected from the group consisting of microorganisms belonging to the genus Brevundimonas, the genus Paracoccus, the genus Sphingomonas, the genus Acidovorax, the genus Pseudomonas, the genus Burkholderia and genetically engineered recombinant microorganisms having ethylenediamine-N,N'-disuccinate ethylenediamine lyase genes from said microorganisms.

17. The method of claim 11 wherein the microorganism having malate isomerase activity is selected from the group consisting of microorganisms belonging to the genus Alcaligenes, the genus Pseudomonas, the genus Xanthomonas, the genus Bacillus and genetically engineered recombinant microorganisms having malate isomerase genes from said microorganisms.

18. The method of claim 11 wherein the matter having ethylenediamine-N,N'-disuccinate ethylenediamine lyase activity processed from a microorganism having ethylenediamine-N,N'-disuccinate ethylenediamine lyase activity is selected from the group consisting of disrupted microbial cells, crude enzyme solution, purified enzyme solution, immobilized microbial ecells, and immobilized enzyme.

19. The method of claim 11 wherein the microorganism having malate isomerase activity is selected from the group consisting of microorganisms belonging to the genus Alcaligenes, the genus Pseudomonas, the genus Xanthomonas, the genus Bacillus and genetically engineered recombinant microorganisms having malate isomerase genes from said microorganisms and the matter having ethylenediamine-N,N'-disuccinate ethylenediamine lyase activity processed from a microorganism having ethylenediamine-N,N'-disuccinate ethylenediamine lyase activity is selected from the group consisting of disrupted microbial cells, crude enzyme solution, purified enzyme solution, immobilized microbial cells, and immobilized enzyme.

20. The method of claim 12 wherein matter having malate isomerase activity processed from a microorganism having malate isomerase activity is selected from the group consisting of disrupted microbial cells, crude enzyme solution, purified enzyme solution, immobilized microbial cells, and immobilized enzyme.

21. A method of claim 12 wherein the microorganism having ethylenediamine-N,N'-disuccinate ethylenediamine lyase activity is selected from the group consisting of genus of Brevundimonas, the genus Paracoccus, the genus Sphingomonas, the genus Acidovorax, the genus Pseudomonas, the genus Burkholderia and genetically engineered recombinant microorganisms having ethylenediamine-N,N'-disuccinate ethylenediamine lyase genes from said microorganisms.

22. The method of claim 12 wherein the matter having malate isomerase activity processed from a microorganism having malate isomerase activity is selected from the group consisting of disrupted microbial cells, crude enzyme solution, purified enzyme solution, immobilized microbial cells, and immobilized enzyme and the microorganism having ethylenediamine-N,N'-disuccinate ethylenediamine lyase activity is selected from the group consisting of microorganisms belonging to the genus Brevundimonas, the genus Paracoccus, the genus Sphingomonas, the genus Acidovorax, the genus Pseudomonas, the genus Burkholderia and genetically engineered recombinant microorganisms having ethylenediamine-N,N'-disuccinate ethylenediamine lyase genes from said microorganisms.

23. The method of claim 13 wherein the matter having malate isomerase activity processed from a microorganism having malate isomerase activity is selected from the group consisting of disrupted microbial cells, crude enzyme solution, purified enzyme solution, immobilized microbial cells, and immobilized enzyme.

24. The method claim 13 wherein the matter having ethylenediamine-N,N'-disuccinate ethylenediamine lyase activity processed from a microorganism having ethylenediamine-N,N'-disuccinate ethylenediamine lyase activity is selected from the group consisting of disrupted microbial cells, crude enzyme solution, purified enzyme solution, immobilized microbial cells, and immobilized enzyme.

25. The method of claim 13 wherein the matter having malate isomerase activity processed from a microorganism having malate isomerase activity is selected from the group consisting of disrupted microbial cells, crude enzyme solution, purified enzyme solution, immobilized microbial cells, and immobilized enzyme and the matter having ethylenediamine-N, N'-disuccinate ethylenediamine lyase activity processed from a microorganism having ethylenediamine-N,N'-disuccinate ethylenediamine lyase activity is selected from the group consisting of the group consisting of disrupted microbial cells, crude enzyme solution, purified enzyme solution, immobilized microbial cells, and immobilized enzyme.

* * * * *